(12) United States Patent
Nelson et al.

(10) Patent No.: US 9,574,183 B2
(45) Date of Patent: Feb. 21, 2017

(54) METHOD AND KITS FOR REPAIRING NUCLEIC ACID SEQUENCES

(75) Inventors: John Richard Nelson, Clifton Park, NY (US); Wei Gao, Clifton Park, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 810 days.

(21) Appl. No.: 13/344,504

(22) Filed: Jan. 5, 2012

(65) Prior Publication Data
US 2012/0107806 A1    May 3, 2012

Related U.S. Application Data

(62) Division of application No. 12/169,399, filed on Jul. 8, 2008.

(51) Int. Cl.
*C12N 9/12*      (2006.01)
*C12N 9/00*      (2006.01)

(52) U.S. Cl.
CPC ............... *C12N 9/1252* (2013.01); *C12N 9/93* (2013.01)

(58) Field of Classification Search
None
See application file for complete search history.

(56) References Cited

U.S. PATENT DOCUMENTS

| | | | |
|---|---|---|---|
| 7,700,283 B2 * | 4/2010 | Evans et al. | 435/6.12 |
| 2001/0039039 A1 | 11/2001 | Weissman et al. | |
| 2005/0069991 A1 | 3/2005 | Hyman | |
| 2005/0084938 A1 * | 4/2005 | Hyman | 435/91.2 |
| 2006/0014154 A1 * | 1/2006 | Eshoo | 435/6 |
| 2007/0010664 A1 | 1/2007 | Thomas et al. | |

FOREIGN PATENT DOCUMENTS

WO     2005017173 A1    2/2005

OTHER PUBLICATIONS

Pusch et al. (Nucleic Acids Research, 1998, 26(3):857-859, IDS reference).*
Grossman et al. (Cold Spring Harb Symp Quant Biol, 1979, 43:947-955).*
Fan, et al., "Protein-protein interactions and posttranslational modifications in mammalian base excision repair", Free Radical Biology and Medicine, Elsevier Science, vol. 38, No. 9, pp. 1121-1138, May 1, 2005.
Zharkov et al., "The DNA trackwalkers: Principles of lesion search and recognition by DNA glycosylases", Mutation Research, Elsevier, vol. 577, No. 1-2, pp. 24-54, Sep. 4, 2005.
PCT Search Report and Written Opinion; Sep. 29, 2009, pp. 1-8.
Beese et al., (EMBO Journal, 1991, 10(1):25-33).
Pusch et al. (Nucleic Acids Research, 1998, 26(3):857-859).
Park et al. (Pharmacogenetic, 2004, vol. 14:103-109).
Dianov et al. (Curr Biol, 1994, 4:1069-1076).

* cited by examiner

*Primary Examiner* — Stephanie K Mummert
(74) *Attorney, Agent, or Firm* — Fletcher Yoder, P.C.

(57) ABSTRACT

Methods and kits for DNA repair are provided. The methods and kits described herein repair multiple types of DNA damage. The kit may include a plurality of enzymes to repair a greater variety of lesions than any single enzyme is capable of repairing. Repair of damaged DNA may include releasing damaged bases from the DNA strand, nicking the DNA at the damaged sites, translating the nicks via 5'-3' exonuclease activity, and sealing the nicks. The enzymes employed in the repair process may then be heat-inactivated, thereby obviating a purification process. The repaired DNA may then be analyzed using a variety of DNA analysis methods.

16 Claims, 5 Drawing Sheets

SEQUENCE LISTING

```
<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: PRIMER

<400> SEQUENCE: 1
ccggaggtaa aggtgtctta aagt                                            24

<210> SEQ ID NO 2
<211> LENGTH: 22
<212> TYPE: DNA
<213> ORGANISM: Artificial Sequence
<220> FEATURE:
<223> OTHER INFORMATION: PRIMER

<400> SEQUENCE: 2
atttcctgtg tcagaccctg tt                                              22

<210> SEQ ID NO 3
<211> LENGTH: 19
<212> TYPE: DNA
<213> ORGANISM: Artificial Sequence
<220> FEATURE:
<223> OTHER INFORMATION: PRIMER
```

```
<400> SEQUENCE: 3
actgcagtcc aatctgggt                                                19

<210> SEQ ID NO 4
<211> LENGTH: 21
<212> TYPE: DNA
<213> ORGANISM: Artificial Sequence
<220> FEATURE:
<223> OTHER INFORMATION: PRIMER

<400> SEQUENCE: 4
atgaaatcaa cagaggcttg c                                             21

<210> SEQ ID NO 5
<211> LENGTH: 23
<212> TYPE: DNA
<213> ORGANISM: Artificial Sequence
<220> FEATURE:
<223> OTHER INFORMATION: PRIMER

<400> SEQUENCE: 5
ggtgattttc ctctttggta tcc                                           23

<210> SEQ ID NO 6
<211> LENGTH: 26
<212> TYPE: DNA
<213> ORGANISM: Artificial Sequence
<220> FEATURE:
<223> OTHER INFORMATION: PRIMER

<400> SEQUENCE: 6
agccacagtt tacaacattt gtatct                                        26

<210> SEQ ID NO 7
<211> LENGTH: 21
<212> TYPE: DNA
<213> ORGANISM: Artificial Sequence
<220> FEATURE:
<223> OTHER INFORMATION: PRIMER

<400> SEQUENCE: 7
atgttggtca ggctgactat g                                             21

<210> SEQ ID NO 8
<211> LENGTH: 24
<212> TYPE: DNA
<213> ORGANISM: Artificial Sequence
<220> FEATURE:
<223> OTHER INFORMATION: PRIMER

<400> SEQUENCE: 8
gattccacat ttatcctcat tgac                                          24

<210> SEQ ID NO 9
<211> LENGTH: 29
<212> TYPE: DNA
<213> ORGANISM: Artificial Sequence
<220> FEATURE:
<223> OTHER INFORMATION: PRIMER

<400> SEQUENCE: 9
gcaacttata tgtatttttg tatttcatg                                     29

<210> SEQ ID NO 10
<211> LENGTH: 28
```

```
<212> TYPE: DNA
<213> ORGANISM: Artificial Sequence
<220> FEATURE:
<223> OTHER INFORMATION: PRIMER

<400> SEQUENCE: 10
accaaattgt gttcatgagt atagtttc                                28

<210> SEQ ID NO 11
<211> LENGTH: 23
<212> TYPE: DNA
<213> ORGANISM: Artificial Sequence
<220> FEATURE:
<223> OTHER INFORMATION: PRIMER

<400> SEQUENCE: 11
acagaagtct gggatgtgga gga                                     23

<210> SEQ ID NO 12
<211> LENGTH: 19
<212> TYPE: DNA
<213> ORGANISM: Artificial Sequence
<220> FEATURE:
<223> OTHER INFORMATION: PRIMER

<400> SEQUENCE: 12
ggcagcccaa aaagacaga                                          19

<210> SEQ ID NO 13
<211> LENGTH: 24
<212> TYPE: DNA
<213> ORGANISM: Artificial Sequence
<220> FEATURE:
<223> OTHER INFORMATION: PRIMER

<400> SEQUENCE: 13
gggggtctaa gagcttgtaa aaag                                    24

<210> SEQ ID NO 14
<211> LENGTH: 29
<212> TYPE: DNA
<213> ORGANISM: Artificial Sequence
<220> FEATURE:
<223> OTHER INFORMATION: PRIMER

<400> SEQUENCE: 14
gtttgtgtgt gcatctgtaa gcatgtatc                               29

<210> SEQ ID NO 15
<211> LENGTH: 20
<212> TYPE: DNA
<213> ORGANISM: Artificial Sequence
<220> FEATURE:
<223> OTHER INFORMATION: PRIMER

<400> SEQUENCE: 15
ttcttgagcc cagaaggtta                                         20

<210> SEQ ID NO 16
<211> LENGTH: 24
<212> TYPE: DNA
<213> ORGANISM: Artificial Sequence
<220> FEATURE:
<223> OTHER INFORMATION: PRIMER

<400> SEQUENCE: 16
```
ctaccagcaa caacacaaat aaac                                              24

<210> SEQ ID NO 17
<211> LENGTH: 22
<212> TYPE: DNA
<213> ORGANISM: Artificial Sequence
<220> FEATURE:
<223> OTHER INFORMATION: PRIMER

<400> SEQUENCE: 17
atatgtgagt caattcccca ag                                                22

<210> SEQ ID NO 18
<211> LENGTH: 26
<212> TYPE: DNA
<213> ORGANISM: Artificial Sequence
<220> FEATURE:
<223> OTHER INFORMATION: PRIMER

<400> SEQUENCE: 18
tgtattagtc aatgttctcc agagac                                            26

<210> SEQ ID NO 19
<211> LENGTH: 20
<212> TYPE: DNA
<213> ORGANISM: Artificial Sequence
<220> FEATURE:
<223> OTHER INFORMATION: PRIMER

<400> SEQUENCE: 19
ggctgcaggg cataacatta                                                   20

<210> SEQ ID NO 20
<211> LENGTH: 23
<212> TYPE: DNA
<213> ORGANISM: Artificial Sequence
<220> FEATURE:
<223> OTHER INFORMATION: PRIMER

<400> SEQUENCE: 20
ttctatgact ttgcgcttca gga                                               23

<210> SEQ ID NO 21
<211> LENGTH: 21
<212> TYPE: DNA
<213> ORGANISM: Artificial Sequence
<220> FEATURE:
<223> OTHER INFORMATION: PRIMER

<400> SEQUENCE: 21
gtgattccca ttggcctgtt c                                                 21

<210> SEQ ID NO 22
<211> LENGTH: 20
<212> TYPE: DNA
<213> ORGANISM: Artificial Sequence
<220> FEATURE:
<223> OTHER INFORMATION: PRIMER

<400> SEQUENCE: 22
tcctgtgggc tgaaaagctc                                                   20

<210> SEQ ID NO 23
<211> LENGTH: 20
<212> TYPE: DNA
<213> ORGANISM: Artificial Sequence

```
<220> FEATURE:
<223> OTHER INFORMATION: PRIMER

<400> SEQUENCE: 23
gcacagaaca ggcacttagg                                                    20

<210> SEQ ID NO 24
<211> LENGTH: 18
<212> TYPE: DNA
<213> ORGANISM: Artificial Sequence
<220> FEATURE:
<223> OTHER INFORMATION: PRIMER

<400> SEQUENCE: 24
cgctcaaacg tgaggttg                                                      18

<210> SEQ ID NO 25
<211> LENGTH: 33
<212> TYPE: DNA
<213> ORGANISM: Artificial Sequence
<220> FEATURE:
<223> OTHER INFORMATION: PRIMER

<400> SEQUENCE: 25
gccctagtgg atgataagaa taatcagtat gtg                                     33

<210> SEQ ID NO 26
<211> LENGTH: 30
<212> TYPE: DNA
<213> ORGANISM: Artificial Sequence
<220> FEATURE:
<223> OTHER INFORMATION: PRIMER

<400> SEQUENCE: 26
ggacagatga taaatacata ggatggatgg                                         30

<210> SEQ ID NO 27
<211> LENGTH: 19
<212> TYPE: DNA
<213> ORGANISM: Artificial Sequence
<220> FEATURE:
<223> OTHER INFORMATION: PRIMER

<400> SEQUENCE: 27
ccctgggctc tgtaaagaa                                                     19

<210> SEQ ID NO 28
<211> LENGTH: 24
<212> TYPE: DNA
<213> ORGANISM: Artificial Sequence
<220> FEATURE:
<223> OTHER INFORMATION: PRIMER

<400> SEQUENCE: 28
atcagagctt aaactgggaa gctg                                               24
```

METHOD AND KITS FOR REPAIRING NUCLEIC ACID SEQUENCES

CROSS-REFERENCE TO RELATED APPLICATIONS

This application is a divisional of patent application Ser. No. 12/169,399, entitled "Method and Kits for Repairing Nucleic Acid Sequences," filed Jul. 8, 2008, which is herein incorporated by reference in its entirety for all purposes.

REFERENCE TO SEQUENCE LISTING SUBMITTED ELECTRONICALLY

The present application contains a Sequence Listing of SEQ ID NOS 1-28 in file "197952-1_sequence_listing_07JUL2008.txt" (5.1 kilobytes), created on Jun. 13, 2008, concurrently submitted with the specification by electronic filing, which is herein incorporated by reference in its entirety.

BACKGROUND

The invention relates generally to forensic analysis, and, more specifically, to repair of damaged nucleic acid sequences.

In criminal investigations, investigators often look for physical evidence left behind at the scene of a crime to link a suspect to the crime. For example, physical evidence has traditionally included fingerprints, hairs, fibers, and so forth. A modern forensic analysis of physical evidence may include analysis of evidence, such as blood or other bodily fluids, which contains deoxyribonucleic acid (DNA) or ribonucleic acid (RNA) specimens. Forensic laboratories analyze DNA and/or RNA samples in an attempt to determine the identity of the person to whom the sample belongs. For example, in criminal forensics, a subject may leave blood or other evidence containing DNA at the scene of the crime. By determining from whom the DNA evidence came, the government can use such evidence in court to prosecute a suspect.

DNA analysis performed at forensic laboratories may be hampered by DNA samples that have been exposed to uncontrolled environmental conditions. Environmentally damaged samples may contain shortened DNA fragments (i.e., double-stranded breaks in the DNA), which are refractive to standard analysis methods, or may contain somewhat intact DNA with single-stranded nicks and lesions. Some examples of damaging exposure include acid and heat exposure, which leads to missing bases and/or apurinic and apyrimidinic sites (AP sites); ionizing radiation and electrophilic agents, including alkylating agents, which modify bases or the sugar backbone; oxidative damage, which leads to altered bases; and UV irradiation, which produces cyclobutane dimers. In the event of such damage, the DNA sample often cannot be analyzed effectively and thus cannot be used as evidence in criminal prosecutions.

BRIEF DESCRIPTION

In certain embodiments, there is provided a DNA repair kit including a thermally labile DNA polymerase having 5'-3' exonuclease activity and a thermally labile DNA ligase.

In other embodiments, there is provided a DNA repair kit having a combination of enzymes, where the combination exhibits N-glycosylase, AP-lyase, 5'-3' DNA polymerase, and 5'-3' exonuclease nick translation activities. The combination of DNA enzymes may be heat inactivable.

There is also provided a DNA repair kit including a DNA glycosylase, a DNA endonuclease, a DNA polymerase I, and a T4 DNA ligase.

Further embodiments provide a method, including incubating damaged DNA with a DNA repair enzyme blend at a first temperature to generate repaired DNA. The DNA repair enzyme blend may include a thermally labile DNA polymerase having 5'-3' exonuclease activity and a thermally labile DNA ligase.

Still further embodiments provide a method, including removing a base from a damaged site on a DNA strand via a glycosylase, nicking the DNA strand at the damaged site via an endonuclease, translating the nick down the DNA strand via a DNA polymerase having an associated 5'-3' exonuclease activity, and sealing the nick with a ligase.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Damaged DNA may contain nucleotide modifications and/or breaks (single- or double-stranded) in the DNA that are a block to the standard DNA replication machinery of the cell. The pathways to the repair of damaged nucleic acids may be broken down into four categories: ligation to seal nicks; direct reversal of a nucleotide modification to normal state; recombinational repair using a second DNA copy as template; and excision repair. The methods described herein may employ enzymes to perform one or more of these repair techniques to repair damaged DNA. Methods for DNA repair described herein may be used, for example, for detection of pathogenic organisms, forensic purposes, medical diagnostic purposes, or clinical purposes. Embodiments are also provided that relate generally to methods applicable in analytical, diagnostic, or prognostic applications.

Figure 1:
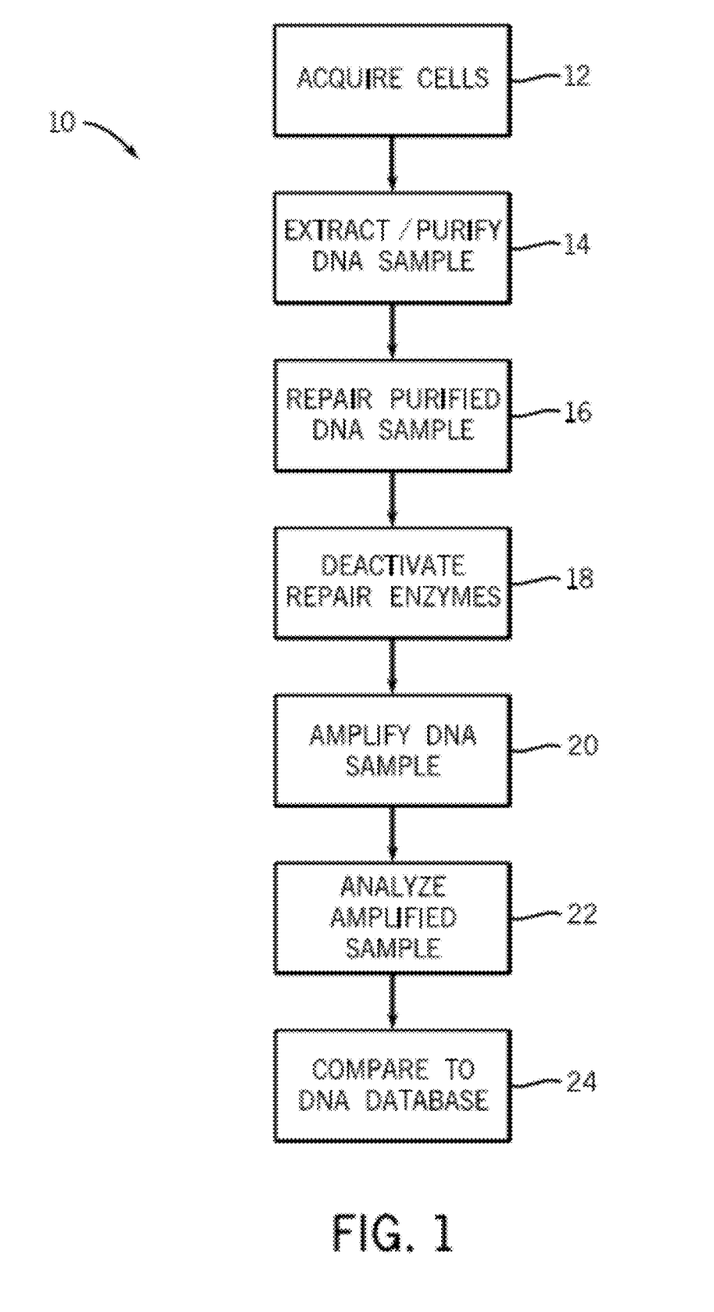
FIG. 1 is a flow chart of a method for analyzing DNA in accordance with aspects of the present technique.

FIG. 1 illustrates an exemplary process 10 by which the methods described herein for DNA repair may be effectively used in analyzing the damaged DNA. Cells containing DNA may be acquired from various sources (block 12). Samples suspected or known to contain DNA may be obtained from a variety of sources, such as, for example, blood or semen samples from a crime scene. The sample may be, but is not limited to, a biological sample, a food or agricultural sample, or an environmental sample. Such samples may be derived from biological tissue, body fluid, or exudate (e.g., blood, plasma, serum or urine, milk, cerebrospinal fluid, pleural fluid, lymph, tears, sputum, saliva, stool, lung aspirates, throat or genital swabs, and the like); whole cells; cell fractions; or cultures. In certain circumstances, it may be desirable to treat the sample to release and/or extract the DNA. A purified DNA sample may be acquired by gently extracting DNA from the cells without denaturing the DNA (e.g., not boiling or using potassium hydroxide) (block 14). Any method for effective extraction and purification of DNA from the source cells may be employed. An exemplary method for DNA purification may be utilization of the illustra tissue and cells genomicPrep Midi Flow Kit, available from GE Healthcare (Catalog No. 28-9042-73).

The extracted DNA may then be repaired by the methods described herein (block 16). The methods for DNA repair are described in greater detail below. As will be demonstrated, the repair method may utilize certain enzymes that can be easily inactivated without denaturing the DNA (block 18). Accordingly, a second purification step may not be required in certain embodiments. The repaired DNA sample may then be amplified (block 20), such as by using isothermal amplification techniques, to increase the amount of sample and facilitate analysis. For example, the repaired DNA may be amplified using a whole genome amplification kit, such as the illustra GenomiPhi DNA Amplification Kit (Catalog No. 25-6600), or a circular amplification kit, such as the illustra TempliPhi™ Amplification Kit (Catalog No. 25-6400), both available from GE Healthcare. Various analysis methods may then be employed to match the DNA sample to an individual (block 22). For example, polymerase chain reaction (PCR) amplification and analysis may be utilized to determine the number of repeating minisatellites at each of thirteen core loci where base pairs are known to repeat uniquely. Other analysis techniques may be employed, such as, for example, amplified fragment length polymorphism (AmpFLP) analysis, short tandem repeats (STR) analysis, or Y-chromosome (Y-STR) analysis. An exemplary quantification analysis technique may employ the Quantifiler™ Human DNA Quantification Kit (Part No. 4343895) available from Applied Biosystems. Analysis produces a unique code, which may be compared to a database of known DNA samples (e.g., the Combined DNA Index System (CODIS) maintained by the Federal Bureau of Investigation (FBI)) (block 24).

For DNA repair (block 16), there are separate classes of protein enzymes that may be used. The first class of enzymes directly repairs damage. This class includes ligase, which seals single-stranded nicks in the double-stranded template, and photolyase, which catalyzes the reversal of certain light-induced damage. A second class of enzymes that may be used for DNA repair operates by identifying base-damaged nucleotides and removing the base section of the nucleotide (e.g., glycosylase activity), leaving an intact sugar backbone. This area of sugar-only backbone is referred to as an apurinic or apyrimidinic (AP) site and is itself a block to replication or amplification. The next class of enzymes includes endonucleases that identify damaged bases and nick the DNA backbone next to the site of damage. In vivo, AP sites may be removed by AP endonucleases. In some cases, the glycosylase activity is associated with an AP endonuclease, and both steps are accomplished by one enzyme. The product of this removal may be either nicked DNA, with the AP site still associated with the strand, or a single base gap with the AP site eliminated. Either product is a block to replication or amplification.

Finally, a nick translation enzyme may also be utilized for DNA repair. In the nick translation process, a DNA polymerase having the ability to both replicate DNA and simultaneously remove blocking single-stranded DNA (e.g., 5'-3' DNA polymerase and 5'-3' exonuclease activities) may be utilized to move down a strand of DNA, essentially eliminating damaged bases in front of it while synthesizing an undamaged version. For the process of nick translation, any DNA polymerase having intrinsic 5'-3' polymerase activity which is functionally coordinated with a 5'-3' exonuclease may be utilized. Classically, this coordination is available using *E. coli* DNA polymerase I; however, any DNA ligase that catalyzes the formation of a phosphodiester bond between juxtaposed 5' phosphate and 3' hydroxyl termini in duplex DNA may be used, including T4 DNA ligase, T7 DNA ligase, and bacterial DNA ligase.

Nick translation by *E. coli* DNA polymerase I is accomplished by simultaneously removing DNA ahead of the enzyme while adding DNA by the polymerase activity. During this process, after a short segment of DNA is replaced by nick translation, the nick translation enzyme dissociates, leaving a nick that may be sealed with ligase. This process is referred to as nick translation because the DNA polymerase is translating a nick down the DNA strand. The process of nick translation may be used to eliminate damaged DNA located to the 5' side of the nick, while simultaneously replacing the damaged nucleotides with an undamaged version. Because the 5'-3' exonuclease activity may be desirable in this repair process, the Klenow fragment (i.e., the large fragment of DNA polymerase I) may not be utilized as the sole polymerase in such embodiments.

The simultaneous use of both the nick translation and ligase enzymes enables completion of short patch repair. Nick translation alone without ligase may result in double-stranded breaks. DNA containing damage on both strands may contain two opposing sites of nick translation. If this occurs, the product of the reaction may be two shorter DNA strands containing a double-stranded DNA break, which is generally undesirable. The inclusion of ligase in the nick translation reaction may prevent double-stranded breakage.

In some embodiments, the repair enzymes are thermally labile and may be permanently inactivated by heating the sample to between 40-80° C. so that the enzymes do not continue functioning during subsequent handling steps where their activity may be inappropriate. When proteins are exposed to increasing temperature, loss of solubility or enzymatic activity may occur over a fairly narrow range. Depending upon the protein studied and the severity of the heating, these changes may not be reversible. As the protein enzyme's tertiary structure is broken, hydrophobic groups are exposed to the solvent in which the enzymes are disposed. The protein may then attempt to minimize its free energy by burying as many hydrophobic groups as possible while exposing as many polar groups as possible to the solvent. While this is analogous to what generally occurs when proteins fold, the much higher temperature may greatly weaken the short-range interaction that initially directs protein folding, and the resulting structures may be vastly different from the native protein. Thus, exposure of many proteins to high temperatures may result in irreversible denaturation.

A combination of enzymes may be employed to simultaneously repair different types of DNA damage. For example, one enzyme may be effective at repairing a particular type of lesion, while another enzyme is preferable for repairing a different lesion. By combining several enzymes into one DNA repair kit, a more robust repair process may be implemented. Exemplary enzymes which may be employed to perform the described functions are listed in Table 1, along with the lesions repaired by each enzyme and the activity performed by each enzyme.

TABLE 1

| Enzyme | Lesion | Activity |
|---|---|---|
| FPG (*E. coli* 8-oxoguanine DNA glycosylase) | 7,8-dihydro-8-oxoguanine (8-oxoguanine)<br>8-oxoadenine<br>Fpy-guanine<br>Methy-fapy-guanine<br>Fapy-adenine<br>Aflatoxin B1-fapy-guanine<br>5-hydroxy-cytosine<br>5-hydroxy-uracil | The N-glycosylase activity releases damaged purines from double-stranded DNA, generating an AP site. The AP-lyase activity cleaves both 3' and 5' to the AP site, thereby removing the AP site and leaving a 1-base gap. |
| Endonuclease IV | Apurinic/apyrimidinic site | AP sites are cleaved at the first phosphodiester bond that is 5' to the lesion, leaving a hydroxyl group at the 3' terminus and a deoxyribose 5'-phosphate at the 5' terminus |
| *E. coli* Endonuclease VIII | Urea<br>5,6-dihydroxythymine<br>Thymine glycol<br>5-hydroxy-5-methylhydanton<br>Uracil glycol<br>6-hydroxy-5,6-dihydrothymine<br>Methyltartronylurea | The N-glycosylase activity releases damaged pyrimidines from double-stranded DNA, generating an AP site. The AP-lyase activity cleaves 3' and 5' to the AP site, leaving a 5' phosphate and a 3' phosphate. |
| T4 Endonuclease V | Cis-syn isomer of cyclobutane pyrimidine dimer | The N-glycosylase activity releases damaged bases from double-stranded DNA, generating an AP site. The associated AP lyase activity nicks the duplex DNA to produce single-strand gaps. |
| *E. coli* DNA polymerase I | N/A | 5"-3" DNA polymerase, 5"-3" exonuclease (nick translation) activity, and 3"-5" exonuclease proofreading activity. |
| T4 DNA ligase | N/A | Joins blunt end and cohesive end termini as well as repairing single-stranded nicks in duplex DNA. |

Figure 2:
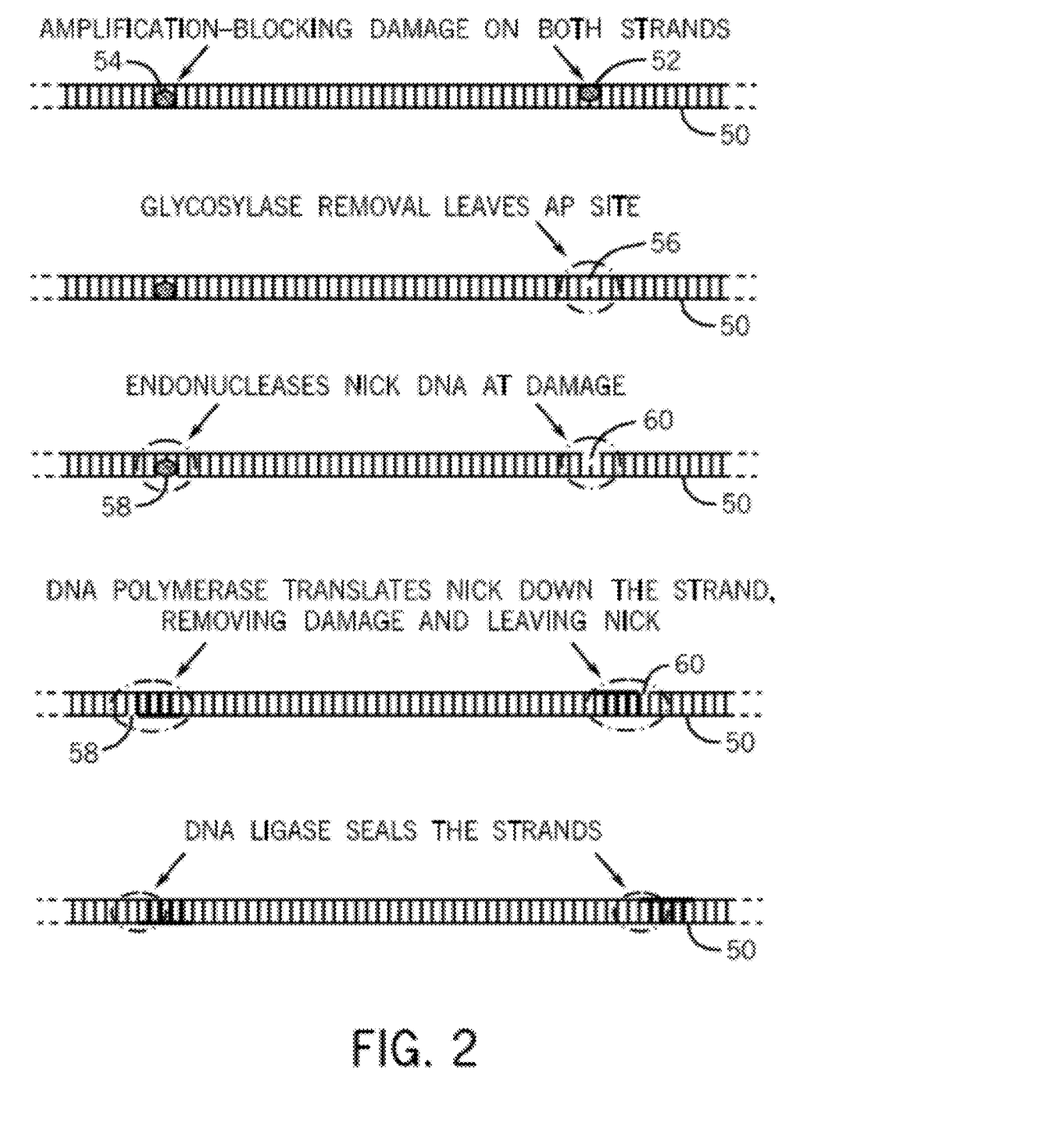
FIG. 2 is a diagrammatical illustration of a method for repairing damaged DNA in accordance with aspects of the present technique.

Turning to FIG. 2, an illustration of the repair of damaged DNA in accordance with the present technique is illustrated. A DNA strand 50 may have one or more damaged (e.g., amplification-blocking) sites 52 and 54. A combination of enzymes may be utilized to perform several repair functions on the DNA strand 50. This combination may include, for example, a glycosylase (e.g., FPG) and/or an endonuclease (e.g., endonuclease IV, endonuclease VII), which removes the damaged base section 52 and leaves an AP site 56. The combination may further include an endonuclease (e.g., T4 endonuclease V) which nicks the DNA at the damaged sites 52 and 54 and/or at the AP site 56, leaving nicks 58 and 60. A DNA polymerase (e.g., *E. coli* DNA polymerase I) included in the combination may then translate the nicks 58 and 60 down the DNA strand 50, repairing the damaged DNA as the nicks 58 and 60 are translated. The nick translation may be accomplished via 5'-3' exonuclease activity. Finally, the nicks 58 and 60 may be sealed with a ligase (e.g., T4 DNA ligase) present in the combination.

It should be understood that the exemplary technique described in reference to FIG. 2 may be carried out via combination of multiple enzymes in a single or multiple mixtures. An exemplary DNA repair kit may include the enzyme mixture described in Table 2.

TABLE 2

| Component | Vendor | Catalog No. | Amout (μl) | Conc. (units/μl) | Final Conc. (units/μl) |
|---|---|---|---|---|---|
| FPG | NEB | M0240 | 1 | 0.08 | 0.008 |
| Endonuclease IV | NEB | M0304 | 1 | 1 | 0.1 |
| *E. coli* Endonuclease VIII | NEB | M0299 | 1 | 1 | 0.1 |

TABLE 2-continued

| Component | Vendor | Catalog No. | Amout (μl) | Conc. (units/μl) | Final Conc. (units/μl) |
|---|---|---|---|---|---|
| T4 Endonuclease V | NEB | M0308 | 1 | 1 | 0.1 |
| RepairBuffer | | | 6 | 1x | |

A 10× preparation of the RepairBuffer solution may include, for example, 100 mM Tris-HCl, 100 mM MgCl$_2$, 500 mM NaCl, and 10 mM dithiothreitol, resulting in a pH of 7.9. The enzymes in the mixture described in Table 2, as well as other enzymes, may be concurrently applied to damaged DNA in a single repair solution. For example, repair of the damaged DNA may be carried out via incubation in a repair solution composed of the mixture described in Table 3.

TABLE 3

| Component | Vendor | Catalog No. | Amout (μl) | Conc. | Final Conc. |
|---|---|---|---|---|---|
| RepairBuffer | | | 3 | 10x | 1x |
| rATP | | | 3 | 10 mM | 1 mM |
| BSA | | | 3 | 1 mg/ml | 0.1 mg/ml |
| dNTP | | | 3 | 2 mM | 0.2 mM |
| *E. coli* Polymerase I | NEB | M0209 | 1 | | |
| T4 DNA Ligase | NEB | M0202 | 1 | | |
| Enzyme Mix (Table 2) | | | 1 | | |

Accordingly, an exemplary DNA repair kit may contain some or all of the components described in Table 3 in either a pre-mixed solution or as separate components available for combination. Approximately 15 µl of damaged DNA may be combined with the repair solution described in Table 3 and incubated at approximately 20-42° C. for 25-60 minutes, then at 42-75° C. for an additional 15-25 minutes. The initial incubation period enables repair of the damaged DNA, while the higher-temperature incubation inactivates the enzymes. In an exemplary embodiment, inactivation of the repair enzymes may be performed by incubating the repaired DNA and enzyme mixture at approximately 65° C. for about 15 minutes. This high-temperature incubation inactivates the thermally labile DNA repair enzymes, including the ligase, without denaturing the repaired DNA. Accordingly, a thermally stable DNA polymerase (e.g., Bst DNA polymerase) and/or a thermally stable DNA ligase (e.g., Taq DNA ligase) may not be desirable, and, in certain embodiments, would not be used in the present process. Furthermore, because certain or all of the enzymes may be heat-inactivatable, purification of the repaired DNA may not be required before amplification.

It should be noted that while the repair solution described in Table 3 includes riboadenosine triphosphate (ribo-ATP), this component may be omitted in practice. In addition, none of the enzymes in the exemplary kit require β-nicotinamide adenine dinucleotide (NAD) to function, and therefore its presence is not necessary.

Once the damaged DNA has been repaired in accordance with presently-described techniques, the repaired DNA may be amplified and analyzed, for example, to determine the identity of the subject from whom the DNA came. As described above, a number of analysis techniques may be employed, including PCR, AmpFLP, STR, Y-STR, and so forth. The heat-inactivated enzymes do not affect the analysis of the DNA and therefore need not be removed from the repaired DNA before proceeding to amplification and analysis.

Experimental Results

Figure 3:
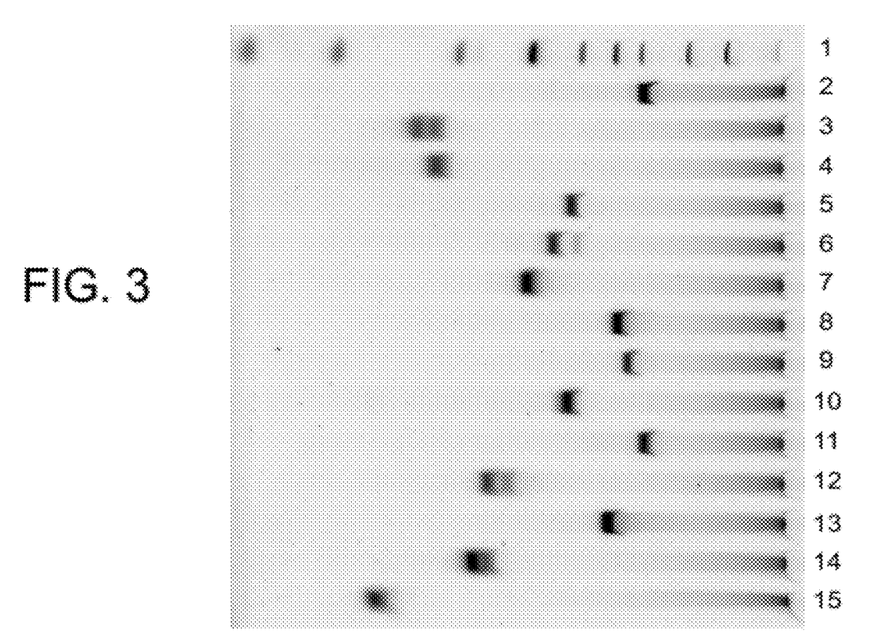
FIG. 3 is an image of a gel run using undamaged DNA.

Genomic DNA was subject to oxidative and ultraviolet damage then repaired in accordance with embodiments of the present technique. The results are summarized below. The genomic DNA for use in the experiments was extracted from the HT29 cell line with a concentration of about 80-160 ng/µl. FIG. 3 is a slide of the undamaged DNA.

In order to damage the DNA, approximately 100 µl of an Fe-EDTA solution that is 9 mM in iron chloride ($FeCl_3$) and 18 mM in EDTA was prepared using 0.37 M $FeCl_3$ and 0.5 EDTA diluted in water. In addition, approximately 1 ml of 30 mM hydrogen peroxide ($H_2O_2$) solution was prepared by adding about 3.4 µl of stock $H_2O_2$ (i.e., 30 percent $H_2O_2$ at approximately 8.8 M) to 1 ml of water. The $H_2O_2$ solution was put on ice.

A reaction mix described in Table 4 was prepared in a tube. The total reaction volume was approximately 30 µl. The $H_2O_2$ solution was added to start the damage reaction. The mix was incubated at 37° C. for various times (e.g., 20-100 min) then desalted using a NAP-5 desalting column, available from GE Healthcare (Catalog No. 17-0853-01), in equilibrium with TE. The mixture was then eluted in 1 ml TE.

TABLE 4

| Components | Volume |
|---|---|
| gDNA(130 ng/ul) | 1 µl |
| Fe-EDTA (9 mM-18 mM) | 5 µl |
| dd H2O | 19 µl |
| 30 mM H2O2 | 4 µl |

Figure 4:
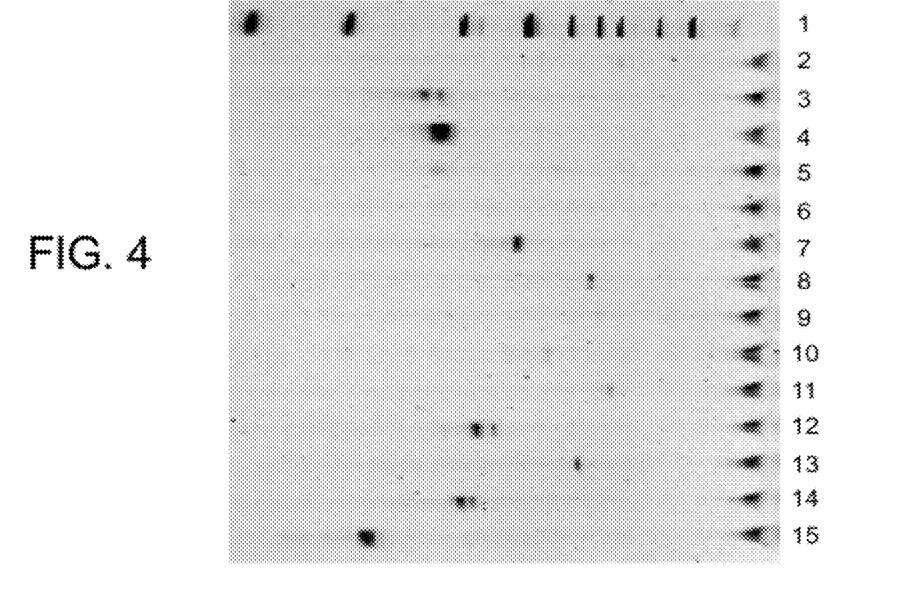
FIG. 4 is an image of a gel run using oxidative damaged DNA.

Oxidative damage DNA samples were prepared using the Fenton reaction. Approximately 2 µl of the genomic DNA extracted from the HT-29 cell line with a concentration of about 130 ng/µl was mixed with 5 µl of the Fe-EDTA solution and 23 µl of double distilled water. About 4 µl of the 30 mM $H_2O_2$ solution was added to start the reaction. Eight tubes of the reaction mixture were prepared and incubated at 37° C. for 80 minutes. The mixtures were then desalted using the NAP-5 desalting column and eluted in 1 ml of TE so that the resulting damaged DNA concentration was about 2 ng/µl. FIG. 4 is a slide of the oxidative damaged DNA.

The oxidative damaged DNA was then combined with a repair mixture containing multiple repair enzymes in a single tube in accordance with embodiments of the present technique. The components of the repair mixture are summarized in Table 5. The repair mixture was incubated at 37° C. for approximately 30 minutes, and then at 65° C. for approximately 20 minutes.

TABLE 5

| Component | Conc. | Amount (µl) | Final Conc. |
|---|---|---|---|
| Repair Buffer | 10 X | 3 | 1 X |
| ATP | 10 mM | 3 | 1 mM |
| dNTP | 1 mM | 3 | 100 µM |
| BSA | 1 mg/ml | 3 | 0.1 mg/ml |
| E. Coli Pol I | 10 U/µl | 1 | 10 U |
| T4 DNA Ligase | 400 U/µl | 1 | 400 U |
| Oxidative Damaged DNA | 2 ng/µl | 15 | 30 ng (approx. 1 ng/µl) |
| Endo IV | 0.1 U/µl | 1 | 0.1 U |
| Endo VIII | 0.1 U/µl | 1 | 0.1 U |
| T4-PDG | 0.1 U/µl | 1 | 0.1 U |

Figure 5:
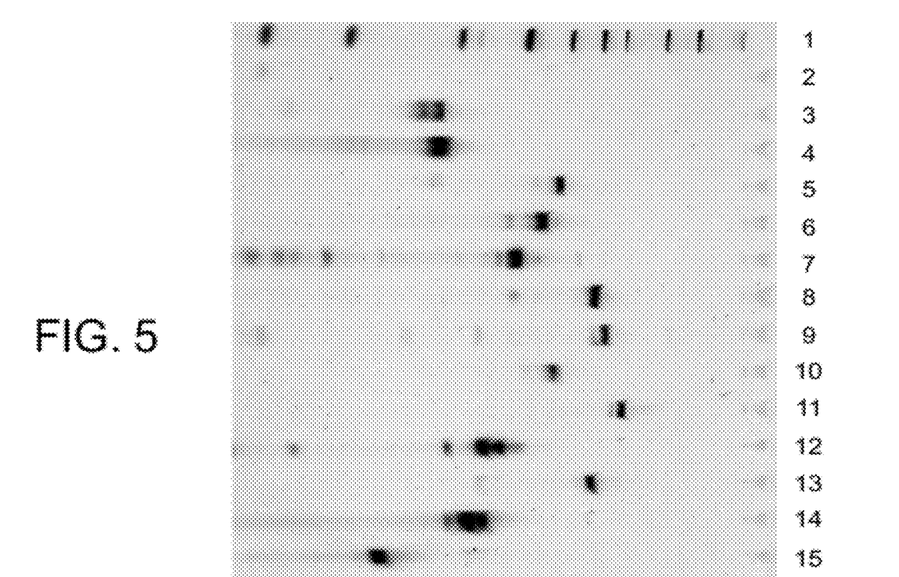
FIG. 5 is an image of a gel run using repaired DNA.

After incubation, PCR amplification was performed on the mixture containing the repaired DNA. The PCR amplification was carried out using the components listed in Table 6. The PCR beads are available from GE Healthcare, Catalog No. 27-9558-01. The PCR amplification was run at 95° C. for 5 minutes; thirty-eight cycles of 95° C. for 30 seconds, 58.5° C. for 30 seconds, and 72° C. for 90 seconds; and 72° C. for 10 minutes. FIG. 5 is a slide of the repaired DNA. Based on these results, the DNA repaired using an embodiment of the presently-disclosed technique (FIG. 5) appears to be closer to the undamaged control DNA (FIG. 3) than is the oxidative damaged DNA (FIG. 4).

TABLE 6

| Components | Conc. | Volume |
|---|---|---|
| Repaired DNA (1 ng/ul) | 1 ng/µl | 2 µl |
| P-Set-14 (2.5 uM) | 2.5 µM | 1.5 µl |
| ddH2O | | 21.5 µl |
| ReadyToGo-PCR beads | | 1 |

Figure 6:
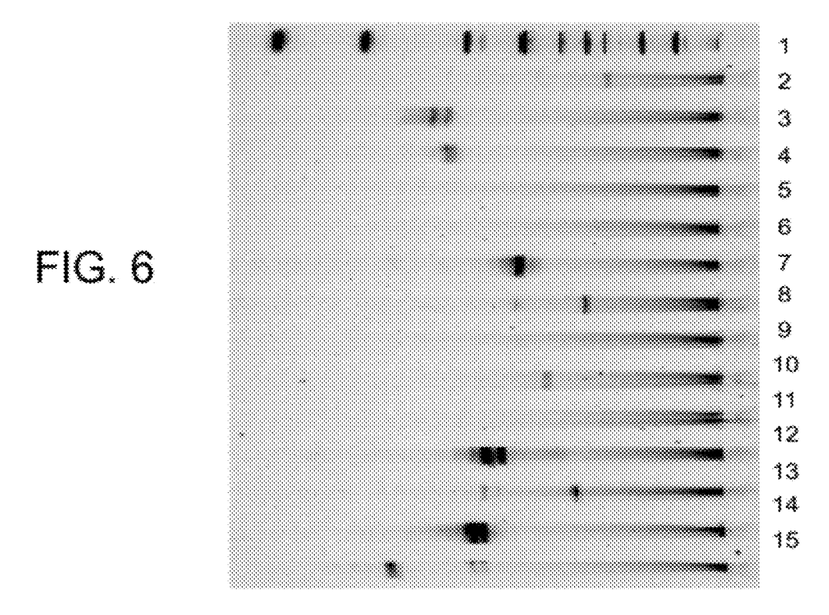
FIG. 6 is an image of a gel run using UV damaged DNA.

In addition to the oxidative damaged samples, UV damaged samples were prepared. Approximately 100 µl of the genomic DNA extracted from the HT-29 cell line with a concentration of about 130 ng/µl was placed in a quartz cuvette and exposed to UVC energy at approximately 245 nm and 4 mW/cm² for 5 minutes. The UV damaged DNA was then diluted to approximately 2 ng/µl. FIG. 6 is a slide of the UV damaged DNA.

The UV damaged DNA was then combined with a repair mixture containing multiple repair enzymes in a single tube in accordance with embodiments of the present technique. The components of the repair mixture are summarized in Table 7. The repair mixture was incubated at 37° C. for approximately 30 minutes, and then at 65° C. for approximately 20 minutes.

TABLE 7

| Components | Conc. | Volume (ul) | Final Conc. |
|---|---|---|---|
| RepairBuffer | 10X | 3 | 1X |
| ATP | 10 mM | 3 | 1 mM |
| dNTP | 1 mM | 3 | 100 µM |
| BSA | 1 mg/ml | 3 | 0.1 mg/ml |
| E. Coli Pol I | 10 U/µl | 1 | 10 U |
| T4 DNA Ligase | 400 U/µl | 1 | 400 U |
| UV Damaged DNA | 2 ng/µl | 15 | 30 ng or ~1 ng/µl |
| EndoIV | 0.1 U/µl | 1 | 0.1 U |
| EndoVIII | 0.1 U/µl | 1 | 0.1 U |
| T4-PDG | 0.1 U/µl | 1 | 0.1 U |

Figure 7:
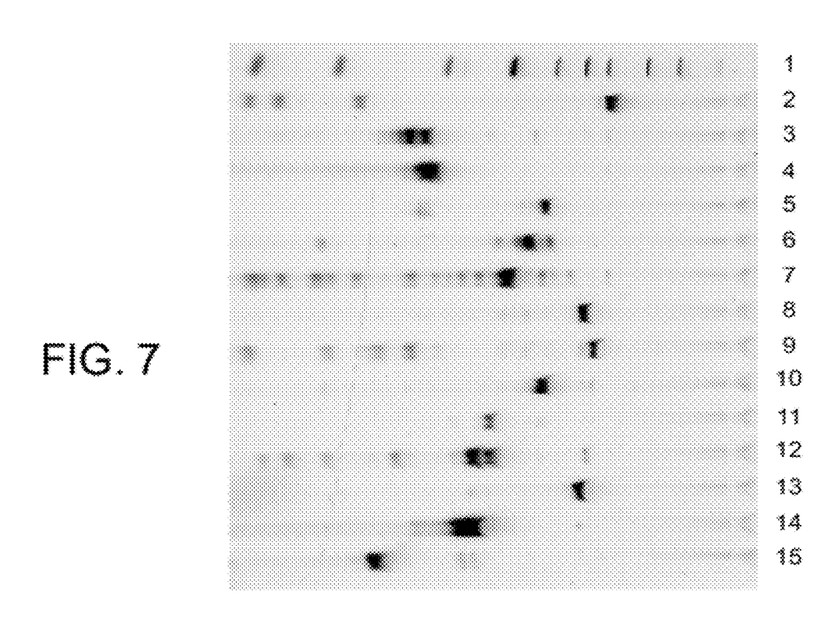
FIG. 7 is an image of a gel run using repaired DNA.

After incubation, PCR amplification was performed on the mixture containing the repaired DNA, as described above. FIG. 7 is a slide of the repaired DNA. Based on these results, the DNA repaired using an embodiment of the presently-disclosed technique (FIG. 7) appears to be closer to the undamaged control DNA (FIG. 3) than is the UV damaged DNA (FIG. 6).

As described above, 2 ng of DNA, damaged DNA, or repaired DNA was amplified by PCR as described using primer sets as indicated in Table 8.

TABLE 8

| Lane on Gel | STR loci | Primer ID | Primer name |
|---|---|---|---|
| 1 | MW marker | | |
| 2 | CSF1PO | Oligo Seq ID 1 | CSF1PO-5'F-1 |
| | | Oligo Seq ID 2 | CSF1PO-3'R-1 |
| 3 | D3S1358 | Oligo Seq ID 3 | D3S1358-5'F |
| | | Oligo Seq ID 4 | D3S1358-3'R |
| 4 | D5S818 | Oligo Seq ID 5 | D5S818-5'F |
| | | Oligo Seq ID 6 | D5S818-3'R |
| 5 | D7S820 | Oligo Seq ID 7 | D7S820-5'F |
| | | Oligo Seq ID 8 | D7S820-3'R |
| 6 | D8S1179 | Oligo Seq ID 9 | D8S1179-5'F |
| | | Oligo Seq ID 10 | D8S1179-3'R |
| 7 | D13S317 | Oligo Seq ID 11 | D13S317-5'F |
| | | Oligo Seq ID 12 | D13S317-3'R |
| 8 | D16S539 | Oligo Seq ID 13 | D16S539-5'F |
| | | Oligo Seq ID 14 | D16S539-3'R |
| 9 | D18S51 | Oligo Seq ID 15 | D18S51-5'F |
| | | Oligo Seq ID 16 | D18S51-3'R |
| 10 | D21S11 | Oligo Seq ID 17 | D21S11-5'F |
| | | Oligo Seq ID 18 | D21S11-3'R |
| 11 | FGA | Oligo Seq ID 19 | FGA-5'F |
| | | Oligo Seq ID 20 | FGA-3'R |
| 12 | TH01 | Oligo Seq ID 21 | TH01-5'F |
| | | Oligo Seq ID 22 | TH01-3'R |
| 13 | TPOX | Oligo Seq ID 23 | TPOX-5'F-1 |
| | | Oligo Seq ID 24 | TPOX-3'R-1 |
| 14 | vWR | Oligo Seq ID 25 | vWR-5'F |
| | | Oligo Seq ID 26 | vWR-3'R |
| 15 | AMEL control (undamaged DNA) | Oligo Seq ID 27 | AMEL-5'F |
| | | Oligo Seq ID 28 | AMEL-3'R |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for repairing damaged genomic DNA, comprising:

incubating damaged genomic DNA with a premixed DNA repair enzyme blend solution at a first temperature to generate repaired genomic DNA, wherein the DNA repair enzyme blend comprises a DNA polymerase having 5'-3' exonuclease activity and a DNA ligase, and wherein a ratio of units of the DNA ligase to units of the DNA polymerase is approximately 40:1 in the premixed DNA repair enzyme blend solution; and inactivating the DNA repair enzyme blend by incubating the repaired genomic DNA and the DNA repair enzyme blend at a second temperature without denaturing the repaired genomic DNA, wherein the second temperature is higher than the first temperature.

2. The method of claim 1, further comprising amplifying the repaired genomic DNA.

3. The method of claim 1, further comprising performing a polymerase chain reaction on the repaired genomic DNA.

4. The method of claim 1, further comprising analyzing the repaired genomic DNA for comparison to a database of known DNA samples.

5. The method of claim 1, wherein the second temperature is in the range of about 42° C. to about 75° C.

6. A method for genomic DNA repair, comprising:
in a single reaction utilizing a DNA repair enzyme blend comprising a glycosylase, an endonuclease, a DNA polymerase, and a ligase at a first temperature to generate repaired genomic DNA by simultaneously performing the steps of:
removing a base from a damaged site on a genomic DNA strand via the glycosylase;
nicking the genomic DNA strand at the damaged site via the endonuclease;
translating the nick down the genomic DNA strand via the DNA polymerase having an associated 5'-3' exonuclease activity; and
sealing the nick with the ligase; and
inactivating the DNA repair enzyme blend by incubating the repaired genomic DNA and the DNA repair enzyme blend at a second temperature without denaturing the repaired genomic DNA, wherein the second temperature is higher than the first temperature.

7. The method of claim 6, wherein the DNA polymerase and the ligase are thermally labile.

8. The method of claim 6, wherein the DNA polymerase comprises both a 5'-3' DNA polymerase activity and a 5'-3' DNA exonuclease activity.

9. The method of claim 1, wherein the damaged genomic DNA comprises oxidatively or ultravioletly damaged DNA.

10. The method of claim 2, wherein the repaired genomic DNA is not purified prior to amplification.

11. The method of claim 3, wherein the repaired genomic DNA is not purified prior to the polymerase chain reaction.

12. The method of claim 4, wherein the repaired genomic DNA is not purified prior to analysis.

13. A method for repairing damaged genomic DNA, comprising:
incubating damaged genomic DNA with a premixed DNA repair enzyme blend solution at a first temperature to generate repaired genomic DNA, wherein the DNA repair enzyme blend simultaneously repairs different types of DNA damage, and the DNA repair enzyme blend comprises at least a DNA polymerase having 5'-3' exonuclease activity, DNA ligase, a glycosylase, and an endonuclease; and
inactivating the DNA repair enzyme blend by incubating the repaired genomic DNA and the DNA repair enzyme blend at a second temperature without denaturing the repaired genomic DNA, wherein the second temperature is higher than the first temperature.

14. The method of claim 13, comprising amplifying the repaired genomic DNA without purifying the repaired genomic DNA.

15. The method of claim 13, comprising performing a polymerase chain reaction on the repaired genomic DNA without purifying the repaired genomic DNA.

16. The method of claim 13, comprising analyzing the repaired genomic DNA for comparison to a database of known DNA samples without purifying the repaired genomic DNA.

* * * * *